(12) United States Patent
Lin et al.

(10) Patent No.: US 8,026,395 B1
(45) Date of Patent: Sep. 27, 2011

(54) PROCESS FOR THE SYNTHESIS OF ANTI-NEOPLASIA AGENT VNP40101M

(75) Inventors: Xu Lin, Branford, CT (US); Ivan King, North Haven, CT (US)

(73) Assignee: Nanotherapeutics, Inc., Alachua, FL (US)

( * ) Notice: Subject to any disclaimer, the term of this patent is extended or adjusted under 35 U.S.C. 154(b) by 304 days.

(21) Appl. No.: 12/454,997

(22) Filed: May 27, 2009

Related U.S. Application Data

(60) Provisional application No. 61/128,975, filed on May 27, 2008.

(51) Int. Cl.
*C07C 303/00* (2006.01)

(52) U.S. Cl. ............................................ 564/81; 564/82

(58) Field of Classification Search .................... 564/81, 564/82
See application file for complete search history.

(56) References Cited

U.S. PATENT DOCUMENTS 4,684,747 A * 8/1987 Sartorelli et al. ............... 564/81

\* cited by examiner

*Primary Examiner* — Jafar Parsa
(74) *Attorney, Agent, or Firm* — Finnegan, Henderson, Farabow, Garrett & Dunner, LLP

(57) ABSTRACT

The present invention relates to simple, safe, high-yield methods of synthesizing VNP40101M, 1,2-bis(methylsulfonyl)-2-(2-chloroethyl)-2-(methylaminocarbonyl)hydrazine, an anti-neoplasia agent. One particularly preferred method uses methyl chloroformamide in a one-pot reaction at elevated temperatures to provide VNP40101M in high yield.

11 Claims, 4 Drawing Sheets

PROCESS FOR THE SYNTHESIS OF ANTI-NEOPLASIA AGENT VNP40101M

RELATED APPLICATIONS

This application claims the benefit of priority of U.S. provisional application Ser. No. 61/128,975, filed May 27, 2008, entitled "Methods of Synthesizing VNP4010M, the entire contents of which are incorporated by reference herein.

FIELD OF THE INVENTION

The present invention relates to novel chemical syntheses of 1,2-bis(methylsulfonyl)-2-2-chloroethyl)-2-(methylaminocarbonyl)hydrazine (VNP40101M), an anti-neoplasia agent.

BACKGROUND OF THE INVENTION

VNP40101M, an anti-neoplasia agent, demonstrates potent anti-tumor activity through alkylation or cross-linking of deoxyribonucleic acid. The compound is classified as a sulfonylhydrazine prodrug, and the proposed mechanism of action suggests formation of a chloroethylating species with a relative specificity for $O^6$-guanine alkylation. An additional decomposition product, methyl isocyanate, may inhibit various DNA repair enzymes (See, Penketh, et al. Biochem Pharmacol 2000, 59(3): 283-291).

A three-step process with a total yield less than 10% has been previously reported published in the following patents and journal articles: U.S. Pat. No. 5,637,619 (Jun. 10, 1997 for VNP40101M); U.S. Pat. No. 4,684,747 (Aug. 4, 1987 for intermediate VNP4090CE); WO97/02029 (Jan. 23, 1997); Journal of Medicinal Chemistry, 1990, 33(8): 2259-2264; Journal of Medicinal Chemistry, 1996, 39(3): 796-801, as illustrated in FIG. 1. 2-Hydroxyethylhydrazine (HEH) was used a starting material and reacted with methanesulfonyl chloride to obtain 1,2-bis(methylsulfonyl)-1-[2-(methylsulfonyloxy)ethyl]hydrazine (BMH) at −20° C. for 18 hours, using pyridine as base. The crude intermediate BMH was treated with lithium chloride in acetone under reflux for 3 days to afford 1,2-bis(methylsulfonyl)-1-(2-chloroethyl)hydrazine (VNP4090CE). After purification by flash column chromatography, an approximately 20% yield was reached for the two steps. VNP4090CE was condensed with methyl isocyanate at room temperature using triethylamine (TEA) as a base. After crystallization from ethanol, 1,2-bis(methylsulfonyl)-1-(2-chloroethyl)-2-(methylcarbamoyl)hydrazine (VNP40101M) with an approximately 42% yield. The total yield of this process was less than 10%. It is noted that the process used methyl isocyanate, which is extremely dangerous for manufacturing in scaleup kilogram amounts. For this reason, the present inventors investigated the synthesis and have developed new methods to prepare VNP40101M.

OBJECTS OF THE INVENTION

It is an object of the invention to provide efficient chemical syntheses for 1,2-bis(methylsulfonyl)-1-(2-chloroethyl)-2-(methylcarbamoyl)hydrazine (VNP40101M).

BRIEF DESCRIPTION OF THE INVENTION

The present invention relates to improved, efficient chemical syntheses for 1,2-bis(methylsulfonyl)-1-(2-chloroethyl)-2-(methylcarbamoyl)hydrazine (VNP40101M).

In the present invention, two efficient syntheses of VNP40101M are provided. In method A of the present invention (FIG. 2), VNP40101M is synthesized from VNP4090CE, phosgene solution and methylamine in a 94% yield. In method B of the present invention (FIG. 3), VNP40101M is synthesized from BMH and methylcarbamic chloride in a 67% yield. The method B of the present invention saves one step to prepare intermediate VNP4090CE. An alternative pathway of method B is shown in FIG. 4.

In the present invention two novel methods relate to syntheses of VNP40101M with higher yields. Method A utilizes a chloroformylating agent to react with VNP4090CE, and then the resulting intermediate reacts with methylamine without separation. Diisopropylethylamine (DIPEA) is used as a base. The white crystal of VNP40101M can be obtained from ethanol crystallization and a higher yield (often as much as 85+%) can be reached, as showed in FIG. 2. In this method, the substituted hydrazine VNP4090CE is chloroformylated and then reacts with methylamine directly, where the chloroformylating agent can be phosgene, trichloromethylchloroformate (triphosgene) or bistrichloromethylcarbonate (diphosgene). The carbonyl coupling reaction of VNP4090CE and methylamine takes place preferably using phosgene-toluene solution. DIPEA is preferably used as a base for the reaction, and acetonitrile is usually used as solvent. The addition of the base into the reaction solution is usually in a temperature below 5° C. then the reaction solution is stirred at room temperature. In the prior art (FIG. 1), product from the mesylation reaction was not isolated and directly used for the chloro-replacement reaction to generate VNP4090CE in an approximately 20% yield. In the instant invention the mesylated product BMH is isolated as a yellow solid in a 55+% yield by easy operations of precipitation and filtration; the chloro-replacement product VNP4090CE is isolated as a white solid in a 85+% yield by easy operations of precipitation and filtration. The yield of the first two-step synthesis can increase to 45+% and the overall yield of the three-step preparation of VNP40101M can be increase to 30+%.

In the present invention two novel methods relate to syntheses of VNP40101M with higher yields. Method B directly uses the intermediate BMH, the starting material for preparation of VNP4090CE. As showed in FIG. 3, a one-pot reaction of BMH with methylcarbamic chloride (MCC) affords VNP40101M in a 60+% yield. In this method, the carbonyl coupling reaction of the substituted hydrazine and the chloro-replacement reaction of the alkyl mesylate take place concurrently. Triethylamine (TEA) is preferably used as a base for the reaction, and acetonitrile is usually used as solvent. The molar ratio of the reactant, BMH to MCC to TEA, is preferable in 1:2:2. The two concurrent reactions are usually heated at approximately 90° C. Other important aspects of the present invention include improvement over the prior art synthesis. In the prior art (FIG. 1), product from the mesylation reaction was not isolated and directly used for the chloro-replacement reaction to generate VNP4090CE in an approximately 20% yield. In the instant invention the mesylated product BMH is isolated as a pale solid in a 55+% yield by easy operations of precipitation and filtration. Thus the total yield of the process to VNP40101M can be increased to 30+%. By the performing this mesylation and two concurrent reactions, the instant invention, in addition to reducing the number of steps required for the synthesis and improving overall yield, also makes handling easier and therefore makes commercial large-scale production easier. Alternatively, the two concurrent reactions in method B were changed to two separation reactions by using an alkyl or aryl chloroformate ClC(O)OR to form a stable carbamade intermediate, followed by a conversion of the carbamade into the corresponding urea (VNP40101M). For example, the reaction of ethyl chloroformate ClC(O)OEt with BMH resulted in a stable intermediate 1,2-bis(methylsulfonyl)-1-(2-chloroethyl)-2-(ethyloxycarbonyl)-hydrazine (CEE), which were reacted with methylamine in the presence of a Lewis acid (preferable $AlCl_3$) to form VNP40101M (FIG. 4). R in ClC(O)OR could be alkyl (e.g. methyl, ethyl, t-butyl, and etc) and aryl (e.g. phenyl, 4-nitrophenyl, and etc). The Lewis acid could be $AlCl_3$, $SnCl_4$, $TiCl_4$, $FeCl_3$, and etc.

In preferred aspects according to the present invention, the present processes have advantage of allowing the preparation of large quantities of VNP40101M without using extremely toxic material like methyl isocyanate (MIC) and providing the final product VNP40101M in high overall yield. The processes of this invention produce high purity anti-neoplasia agent VNP40101M in yields amenable to scale-up and commercial preparation. The present methods address the relatively low yields of the prior art methods and make commercialization of VNP40101M safely and economically viable.

DETAILED DESCRIPTION OF THE INVENTION

The term "neoplasia" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to reduce after attempted removal and to cause the death of the patient unless adequately treated. As used therein, the term neoplasia is used to describe all cancerous disease states and embraces or encompasses the pathological process associated with malignant hematogeous, ascitic and solid tumors.

The term "alkyl" refers to an optionally substituted (unsubstituted or substituted with a group which is inert to reaction conditions, but usually facilitates the reaction, e.g., a nitro group or other electron withdrawing group) fully saturated hydrocarbon group, which may be linear, branched or cyclic containing from 1 to 15 carbon atoms, preferably 1 to 10 carbon atoms, more preferably 1 to 6 carbon atoms.

The term "aryl" refers to a phenyl or naphthyl group, which is optionally substituted with a group which is inert to reaction conditions, but usually facilitates the reaction (e.g., a nitro group or other electron withdrawing group or a halogen, especially Br, F, Cl).

Figure 1:
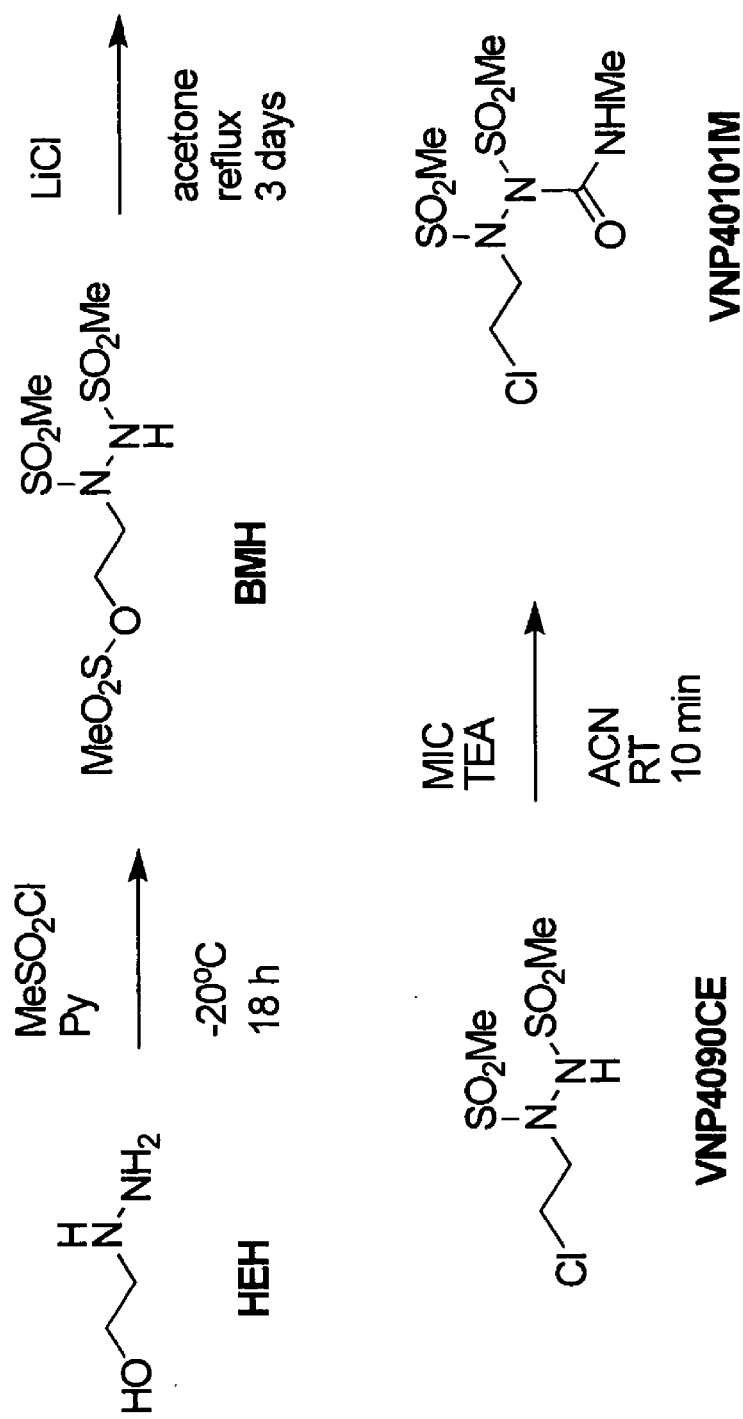
FIG. 1 represents the prior art synthesis of VNP40101M using methyl isocyanate through BMH and VNP4090CE intermediates. The three-step synthesis proceeds to completion in a total yield of less than 10%.
Figure 2:
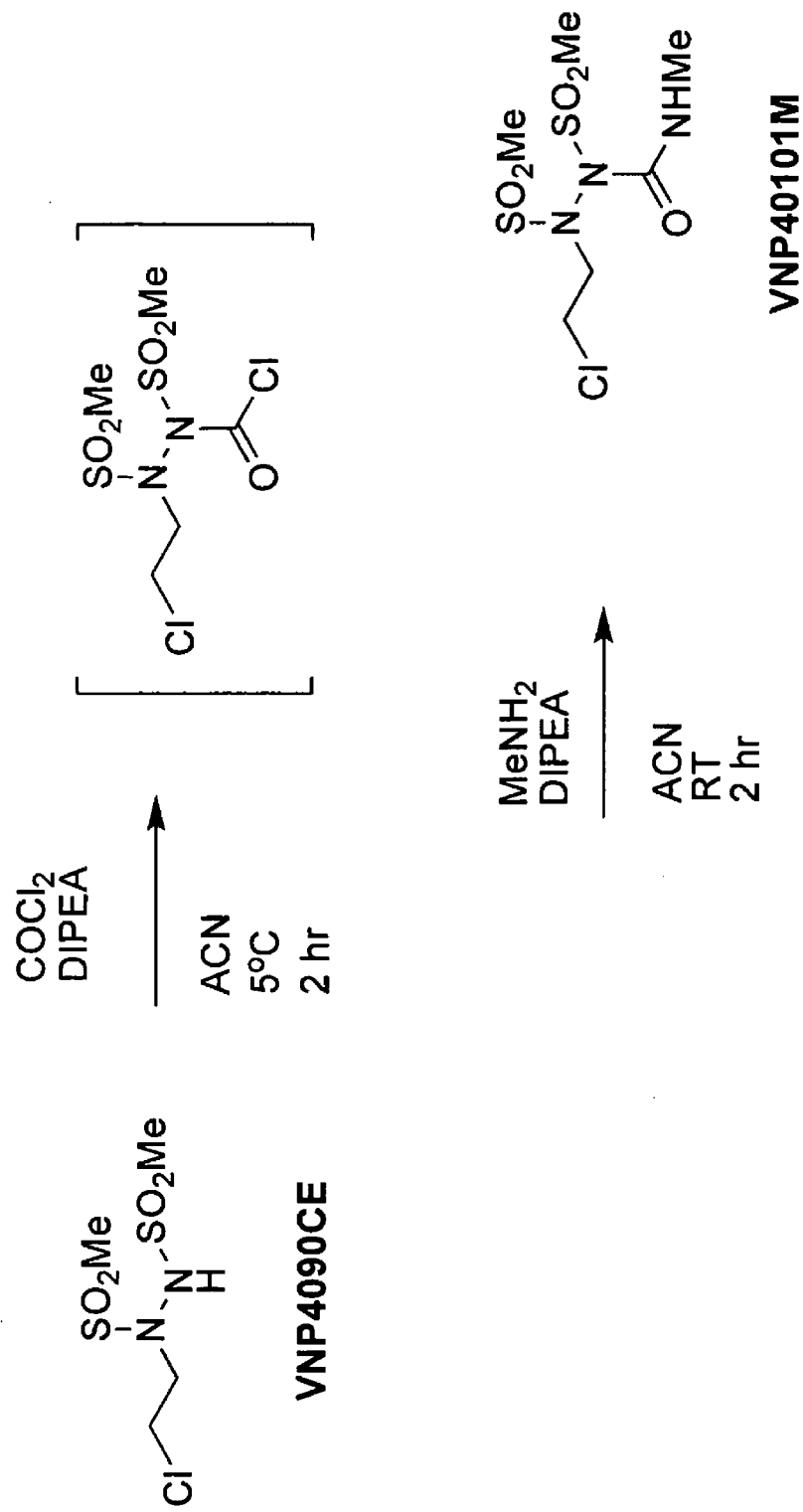
FIG. 2 provides a novel synthesis of VNP40101M using phosgene and methylamine through BMH and VNP4090CE intermediates. The three-step synthesis proceeds to completion in a total yield of more than 30%.
Figure 3:
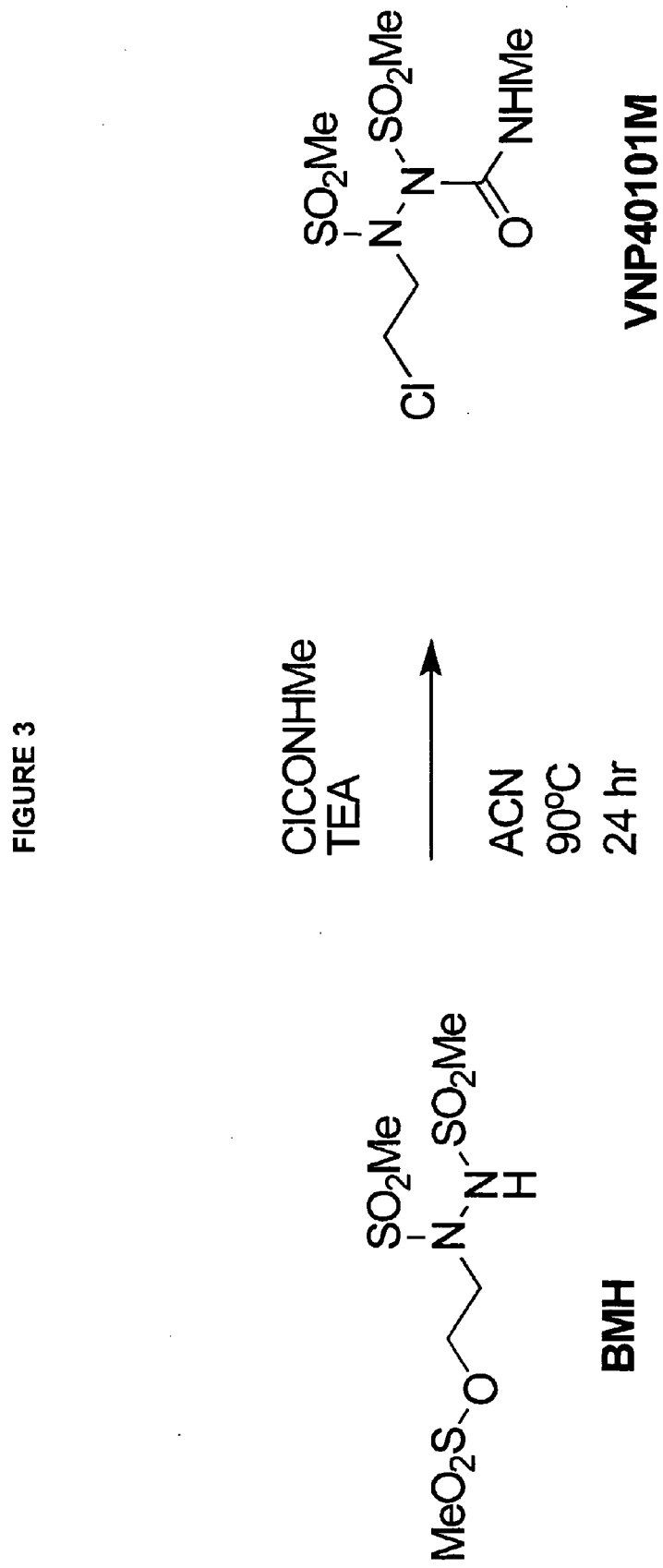
FIG. 3 provides a novel synthesis of VNP40101M using methylcarbamic chloride through BMH intermediate. The two-step synthesis proceeds to completion in a total yield of more than 30%.
Figure 4:
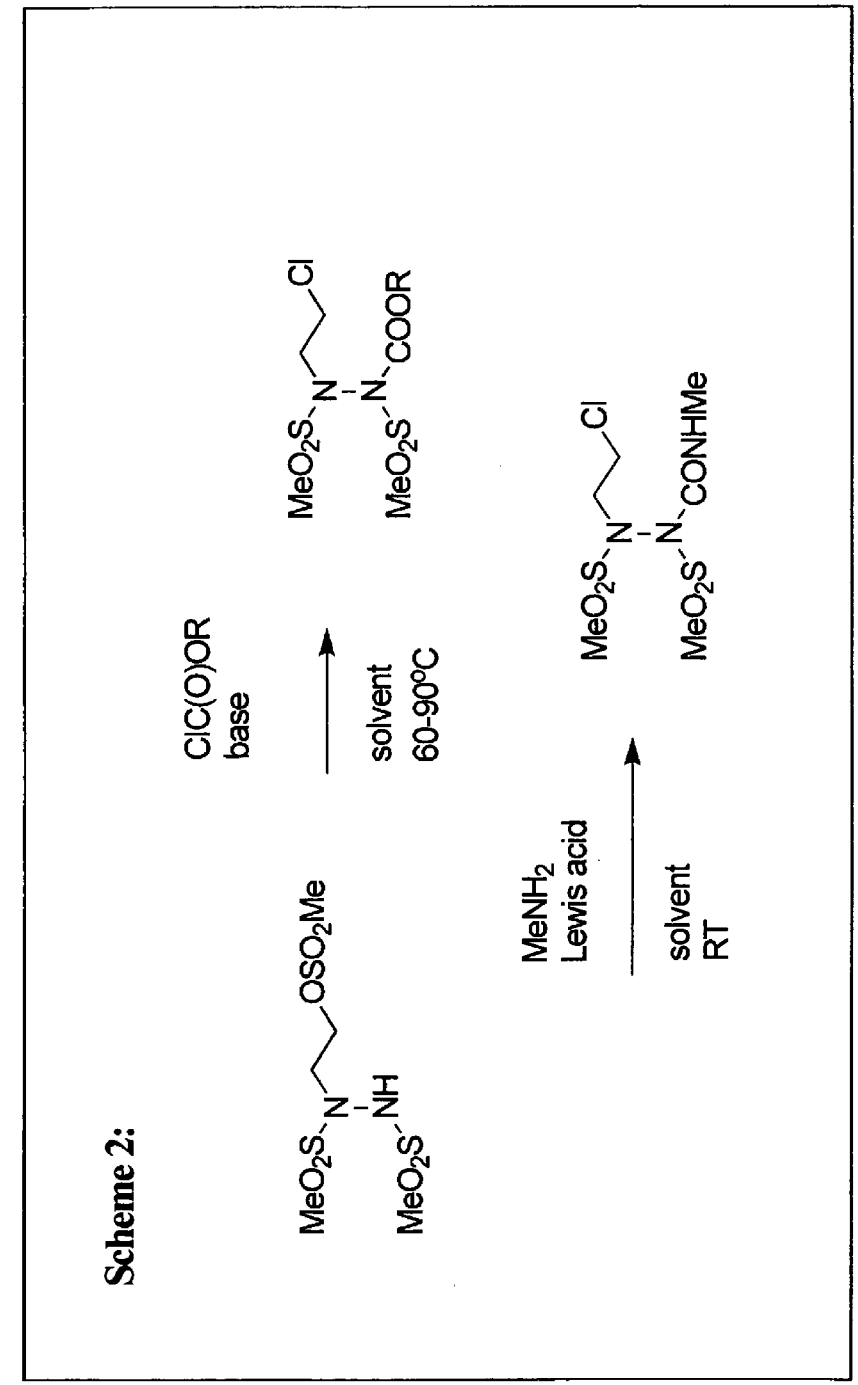
FIG. 4 provides a novel synthesis of VNP40101M using an aryl or aryl chloroformate through BMH intermediate. The three-step synthesis proceeds to completion in a total yield of more than 30%.

The improved syntheses of VNP40101M of the present invention, having higher yields and being safer and more easily performed, are outlined in FIGS. 2 and 3, respectively. The method A was developed for the synthesis of VNP40101M as set forth in FIG. 2. Advantageously, the first two steps in the prior art procedure were improved by using convenient operations, precipitation and filtration, and the yields were increased. Avoided to use methyl isocyanate in the prior art procedure, phosgene toluene solution was used to react with the hydrazine VNP4090CE, and the resulting active intermediate of a hydrazinecarbonyl chloride was directly treated with methylamine to generate VNP40101M, which was crystallized from ethanol without a purification with flash column chromatography in the prior art procedure. The general procedures of method A provided VNP40101M in good yields. Method B was developed for the synthesis of VNP40101M as set forth in FIG. 3. Especially, a one-pot reaction can be established if using methyl chloroformamide at a higher temperature. Advantageously, the number of steps in the prior art procedure (see FIG. 1) was reduced by elimination of the preparation of VNP4090CE from BMH of the prior art synthesis. The mesyloxyethyl hydrazine was directly converted to chloroethylhydrazine while the coupling reaction of methylcarbamic chloride with the substituted hydrazine BMH at a higher temperature, approximately 90° C. The general procedures of method B provided VNP40101M in good yields. The purity of VVP40101M can be increased by one or more rounds of ethanol crystallizations.

While the preferred synthetic chemical method has been described above, one of ordinary skill in the art will recognize that substitute or equivalent steps may be used to obtain the same results. For example, one of ordinary skill may readily substitute for certain of the reagents or reagent combination and virtually all of the solvents used to produce an intermediate as set forth in the various schemes. Phosgene, for example, may be readily substituted by any appropriate chloroformylating agent, including diphosgene or triphosgene or phoxime resin.

The present invention now described, purely by way of illustration, in the following examples. It will be understood by one of ordinary skill in the art that these examples are in no way limiting and that variations of detail can be made without departing from the spirit and scope of the present invention.

EXAMPLES

The detailed reaction conditions and characterizations of each compound in the following procedures are provided in this section. All NMR spectra were measured at 300 MHz for 1H on Bruker 300 MHz NMR spectrometer or ACF 300 MHz NMR spectrometer. Chemical shifts (5) were expressed as ppm downfield relative to tetramethylsilane (TMS), and coupling constants (J) were expressed in Hertz (Hz). Mass spectrum analysis (MS) was conducted at Agilent 1100 series LC/MSD Trap (SL) mass spectrometer. Infrared analysis (1R) was determined at Nicolet Impact 410 Infrared spectrometer.

Synthesis of Compound BMH

2-Hydroxyethylhydrazine (HEH, 100 g) was dissolved in dichloromethane (DMC, 750 mL, 7.5±0.5 mL per g of HEH) and pyridine (343 mL, 3.43±0.05 mL per g of HEH). A solution of methanesulfonyl chloride (340 mL, 3.36±0.05 mL per g of HEH) in DCM (100 mL, 1.0±0.5 mL per g of HEH) was slowly added into the stirred solution on a cold bath (below −10° C.) over 20 min by maintaining the reaction temperature below 0° C. Allowed to arise the reaction to room temperature after addition and then keep stirring for 48-72 hr. The reaction completion was monitored by thin layer chromatography (TLC) and an in-process test with $^1$H NMR. After adding 1N HCl solution (1,500 mL, 15±1 mL per g of HEH) into the mixture on an ice bath, a precipitate was formed and filtered. The cake was triturated in ethanol for 2 hr at room temperature, and then filtered. After drying under vacuum the intermediate 1,2-bis(methylsulfonyl)-1-(2-mesyloxyethyl)-hydrazine (BMH) was obtained as yellow solids in a yield of 58%. $^1$H NMR spectrum (300 MHz) was clean: DMSO-$d_6$, δ 9.97 (s, 1H), 4.40 (t, J=5.7 Hz, 2H), 3.70 (br, 2H), 3.19 (s, 3H), 3.12 (s, 3H), and 3.06 (s, 3H). TLC: developed with 80% ethyl acetate in petroleum ether and visualized by spraying a solution of methanol/water/sulfuric acid (3:3:1, v/v/v) Rf=0.60-0.70.

Synthesis of Compound VNP4090CE

A solution of BMH (237 g) and lithium chloride (131 g, 0.55±0.03 g per g of BMH) in N,N-dimethylformamide (DMF, 1,085 mL, 5.0±0.2 mL per g of BMH) was heated on 60° C. bath for 16-24 hr. The reaction completion was monitored by thin layer chromatography (TLC) and an in-process test with $^1$H NMR. After cooling on an ice-bath, water (2,300 mL, 20±1 mL per g of BMH) was added into the reaction mixture, and the mixture was kept stirring. A precipitate was formed and filtered. The cake was triturated in hexanes for 2 hr at room temperature, and then filtered. After drying under vacuum the intermediate 1,2-bis(methylsulfonyl)-1-(2-chloroethyl)-hydrazine (VNP4090CE) was obtained as pale solids in a yield of 88%. $^1$H NMR spectrum (300 MHz) was clean and identical to the compound described in the prior art procedure: DMSO-$d_6$, δ 9.94 (s, 1H), 3.80 (t, J=6.4 Hz, 2H), 3.65 (br, 2H), 3.13 (s, 3H), and 3.06 (s, 3H). Melting point (Capillary tube): 133-135° C. TLC: developed with 60% ethyl acetate in petroleum ether and visualized by spraying a solution of methanol/water/sulfuric acid (3:3:1, v/v/v) Rf=0.60-0.70.

Synthesis of Compound CEE

Procedure 1: A solution of VNP4090CE (40.2 g, 0.16 mol) and triethylamine (TEA, 83.6 mL, 0.60 mol) in acetonitrile (600 mL) was cooled in an ice-bath. After addition of ethyl chloroformate (45.7 mL, 0.48 mol), the reaction mixture was stirred in the ice-bath for 1 hour then at room temperature overnight. A white precipitate was filtered off and the filtrate was evaporated. The residue was dissolved in ethyl acetate (100 mL), and the solution was washed with water and brine. The separated organic layer was dried over magnesium sulfate and evaporated. Then, the oily residue was purified by flash column chromatography, and the product was eluted with 1% v/v MeOH-in-DCM. After removal of the solvents, the resulting solids of CEE were recrystallized with MeOH, and the product solids were dried in vacuum. Yield: 30.6 g (59%).

Procedure 2: Ethyl chloroformate (19.1 mL, 0.20 mol) and TEA (28 mL, 0.20 mol) was dropwise added into a solution of BMH (21.2 g, 0.10 mol) in acetonitrile (250 mL) at room temperature. The reaction solution was stirred at room temperature for 10 min and then heated at 90° C. overnight. After cooling to ambient temperature, the solution was concentrated; the residue was then dissolved in ethyl acetate and washed with 5% HCl solution and brine. The organic phase was dried over anhydrous MgSO$_4$. After filtration, evaporation and drying in vacuum, pure 1,2-bis(methylsulfonyl)-1-(2-chloroethyl)-2-(ethoxycarbonyl)hydrazine (CEE) was obtained. Yield: 20.4 g (63%).

$^1$H NMR spectrum (300 MHz) was clean: CDCl$_3$, δ 4.40 (q, J=7.0 Hz, 2H), 3.83-3.97 (m, 2H), 3.71 (t, J=7.0 Hz, 2H), 3.44 (s, 3H), 3.14 (s, 3H), and 1.38 (t, J=7.0 Hz, 3H). Melting point (Capillary tube): 82-83° C. MS (+Q1) scans: m/z 344.9 (M+Na) and 361.8 (M+K).

Synthesis of Compound VNP40101M by Method A

VNP4090CE (520 g) was dissolved in acetonitrile (5,200 mL, 10±1 mL per g of VNP4090CE) and placed on a cold bath (−8 to −15° C.). A commercially available 20% phosgene toluene solution (1,170 mL, 2.255±0.020 mL per g of VNP4090CE) and diisopropylethylamine (DIPEA, 387 mL, 0.745±0.015 mL per g of VNP4090CE) were added into the stirred VNP4090CE solution. The reaction mixture was kept stirring at below 0° C. for 30 min. A 2.0N methylamine tetrahydrofuran (THF) solution (1,240 mL, 2.375±0.075 mL per g of VNP4090CE) and another portion of DIPEA (387 mL, 0.745±0.015 mL per g of VNP4090CE) were then added. The reaction mixture was stirred at below 0° C. for 1 hr and at room temperature for another 60-90 min. The reaction completion was monitored by thin layer chromatography (TLC) and high-performance liquid chromatography with ultraviolet detector (HPLC/UV). After evaporation to remove solvents, the residue was worked up with brine and DCM twice. The organic phases were combined and dried over anhydrous Na$_2$SO$_4$. After filtration and concentration, the crude product was crystallized in ethanol. After filtration and drying under vacuum, the product 1,2-bis(methylsulfonyl)-1-(2-chloroethyl)-2-[methylamino)carbonyl]-hydrazine (VNP40101M) was obtained as white solids in a yield of 94%. Purity of VNP40101M could be reached to 97% by using one more than one rounds of ethanol solubilization and crystallization steps.

Synthesis of Compound VNP40101M by Method B

BMH (635 g) and methylcarbamic chloride (383 g, 0.602±0.015 g per g of BMH) were dissolved in acetonitrile (6,350 mL, 10±1 mL per g of BMH). Triethylamine (TEA, 570 mL, 0.90±0.1 mL per g of BMH) was added into the solution at room temperature in small portions over 20 min. The reaction mixture was heated at reflux (approximately 90° C.) for 24-36 hr. After cooling to ambient temperature, solvents were evaporated; the residue was worked up with brine and DCM twice. The organic phases were combined and dried over anhydrous Na$_2$SO$_4$. After filtration and concentration, the crude product was crystallized in ethanol. After filtration and drying under vacuum, the product 1,2-bis(methylsulfonyl)-1-(2-chloroethyl)-2-(methylcarbornyl)-hydrazine (VNP40101M) was obtained as white solids in a yield of 67%. Purity of VNP40101M could be reached to 97% by using one more than one rounds of ethanol solubilization and crystallization steps.

Synthesis of Compound VNP40101M by Method C

A 2.0N methyamine THF solution (87 mL, 175 mmol) was slowly added into a suspension of AlCl$_3$ (12 g, 91 mmol) in DCM (40 mL) on an ice-bath over 20 min, maintaining the temperature at below 15° C. A solution of CEE (22.4 g, 70 mmol) in DCM (30 mL) was added into the above methylamine solution in portions at room temperature. The reaction mixture was stirred at room temperature overnight. After quenching with ice water (50 mL), the mixture was stirred for further 1 hr and the resulting suspension was filtered through Celite pad. After separation and extraction, the organic phases were then combined and dried over anhydrous Na$_2$SO$_4$. After filtration and concentration, the crude product was crystallized in ethanol. After filtration and drying under vacuum, the product 1,2-bis(methylsulfonyl)-1-(2-chloroethyl)-2-(methylcarbornyl)-hydrazine (VNP40101M) was obtained as white solids in a yield of 68%. Purity of VNP40101M could be reached to 97% by using one more than one rounds of ethanol solubilization and crystallization steps.

The product VNP40101M obtained by method A or method B above were consistent with the compound described in the prior art procedure. $^1$H NMR spectrum (300 MHz) was clean: DMSO-d$_6$, δ 7.10 (bs, 1H), 3.95 (m, 2H), 3.83 (m, 2H), 3.53 (s, 3H), 3.30 (s, 3H), and 2.68 (d, J=4.2 Hz, 3H). CDCl$_3$, δ 6.42 (bs, 1H), 4.04-3.75 (m, 4H), 3.49 (s, 3H), 3.22 (s, 3H), and 2.88 (d, J=4.8 Hz, 3H). Melting point (Capillary tube): 150-152° C. TLC: developed with 4% ethyl acetate in dichloromethane and visualized by spraying a solution of methanol/water/sulfuric acid (3:3:1, v/v/v) Rf=0.60-0.70. MS (m/z): 308 (M+H) and 330 (M+Na). IR (cm$^{-1}$): 1706, 3047, 3008, and 2935.

It is to be understood that the examples and embodiments described hereinabove are for the purposes of providing a description of the present invention by way of example and are not to be viewed as limiting the present invention in any way. Various modifications or changes that may be made to that described hereinabove by those of ordinary skill in the art are also contemplated by the present invention and are to be included within the spirit and purview of this application and the following claims.

We claim:
1. A method for producing a compound of the formula:

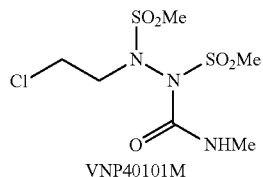
VNP40101M comprising subjecting a compound of the formula:

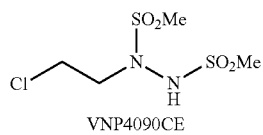
VNP4090CE to a chloroformylating reaction to produce a reactive intermediate of the formula

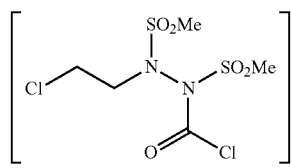

which is subjected to a methylaminylating reaction to produce VNP40101M, said method optionally further purifying VNP40101M to a purity higher than 97% by subjecting said VNP40101M produced to at least one round of ethanol solubilization and crystallization.

2. The method according to claim 1 where the chloroformylating agent is phosgene.

3. The method according to claim 1 where the chloroformylating agent is trichloromethylchloroformate (triphosgene).

4. The method according to claim 1 where the chloroformylating agent is bistrichloromethylcarbonate (diphosgene).

5. The method according to claim 1 for producing a compound of the formula:

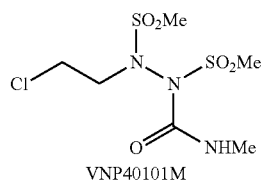
VNP40101M at a purity higher than 97% by subjecting said compound produced according to the method of claim 1 to one or more than one ethanol rounds of solubilization and crystallization steps.

6. A method for producing a compound of the formula:

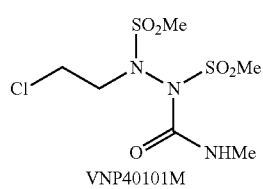
VNP40101M comprising subjecting a compound of the formula:

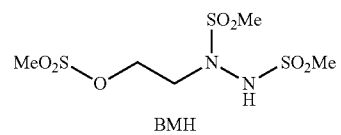
BMH to a reaction with ClCONHMe to produce VNP40101M, said method optionally further purifying VNP40101M to a purity higher than 97% by subjecting said VNP40101M produced to at least one round of ethanol solubilization and crystallization.

7. The method according to claim 6 wherein VNP40101M is produced at a purity higher than 97% by subjecting said VNP40101M to at least one round of ethanol solubilization and crystallization.

8. A method for producing a compound of the formula:

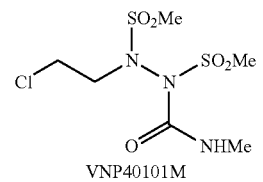
VNP40101M comprising subjecting a compound of the formula:

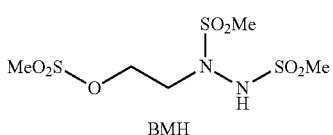
BMH to a reaction with ClC(O)OR to produce a carbamate of the formula:

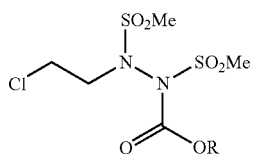

which is subjected to a methylaminylating reaction containing methylamine and a Lewis acid to produce VNP40101M, said method optionally further purifying VNP40101M to a purity higher than 97% by subjecting said VNP40101M produced to at least one round of ethanol solubilization and crystallization.

9. The method according to claim 8 where the R in ClC(O)OR is an alkyl.

10. The method according to claim 8 where the R in ClC(O)OR is an aryl.

11. The method according to claim 8 for producing a compound of the formula:

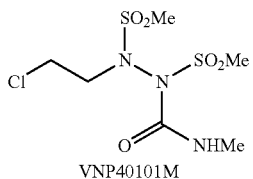
VNP40101M at a purity higher than 97% by using one more than one rounds of ethanol solubilization and crystallization steps.

* * * * *